United States Patent
Sun

(10) Patent No.: US 10,078,123 B2
(45) Date of Patent: Sep. 18, 2018

(54) SYSTEM AND METHOD FOR CORRECTING INTRINSIC HETEROGENEITY IN MAGNETIC RESONANCE IMAGING

(71) Applicant: THE GENERAL HOSPITAL CORPORATION, Boston, MA (US)

(72) Inventor: Phillip Zhe Sun, Waltham, MA (US)

(73) Assignee: The General Hospital Corporation, Boston, MA (US)

( * ) Notice: Subject to any disclaimer, the term of this patent is extended or adjusted under 35 U.S.C. 154(b) by 154 days.

(21) Appl. No.: 15/301,872

(22) PCT Filed: Apr. 17, 2015

(86) PCT No.: PCT/US2015/026303
§ 371 (c)(1),
(2) Date: Oct. 4, 2016

(87) PCT Pub. No.: WO2015/161156
PCT Pub. Date: Oct. 22, 2015

(65) Prior Publication Data
US 2017/0023658 A1    Jan. 26, 2017

Related U.S. Application Data

(60) Provisional application No. 61/981,471, filed on Apr. 18, 2014.

(51) Int. Cl.
| | |
|---|---|
| *G01V 3/00* | (2006.01) |
| *G01R 33/563* | (2006.01) |
| *A61B 5/055* | (2006.01) |
| *A61B 5/00* | (2006.01) |
| *G01R 33/565* | (2006.01) |
| *G01R 33/56* | (2006.01) |

(52) U.S. Cl.
CPC ...... *G01R 33/56341* (2013.01); *A61B 5/0042* (2013.01); *A61B 5/0055* (2013.01); *A61B 5/055* (2013.01); *G01R 33/565* (2013.01); *G01R 33/5608* (2013.01)

(58) Field of Classification Search
CPC ................................. G01R 33/56341
USPC ....................... 324/306, 307, 309
See application file for complete search history.

(56) References Cited

U.S. PATENT DOCUMENTS

| | | | |
|---|---|---|---|
| 7,643,863 B2 | 1/2010 | Basser et al. | |
| 8,278,925 B2 | 10/2012 | Sun et al. | |
| 8,452,373 B2 | 5/2013 | Wyrwicz et al. | |

(Continued)

OTHER PUBLICATIONS

International Search Report and Written Opinion dated Jul. 24, 2015 for International Application No. PCT/US2015/026303.

*Primary Examiner* — Louis Arana
(74) *Attorney, Agent, or Firm* — Quarles & Brady LLP

(57) ABSTRACT

A system and method acquiring images of a region of interest (ROI) of a subject using a magnetic resonance imaging system. The system or method are capable of acquiring pathological data from tissue in the ROI believed to be pathological tissue and acquiring baseline data from tissue in the subject believed to not be pathological tissue. The system or method are also capable of determining correlation parameters from baseline data, generating corrected data using the baseline correlation parameters to correct the pathological data at least for intrinsic heterogeneity, and generating a report using the corrected data.

20 Claims, 10 Drawing Sheets

(56) References Cited

U.S. PATENT DOCUMENTS

| | | |
|---|---|---|
| 9,053,534 B2* | 6/2015 | Ross .................. G06T 7/0012 |
| 2008/0108894 A1 | 5/2008 | Elgavish et al. |
| 2012/0002851 A1 | 1/2012 | Jensen et al. |
| 2016/0260211 A1* | 9/2016 | Gillies ................. G06T 7/41 |
| 2017/0103525 A1* | 4/2017 | Hu ..................... G06T 7/0012 |

* cited by examiner

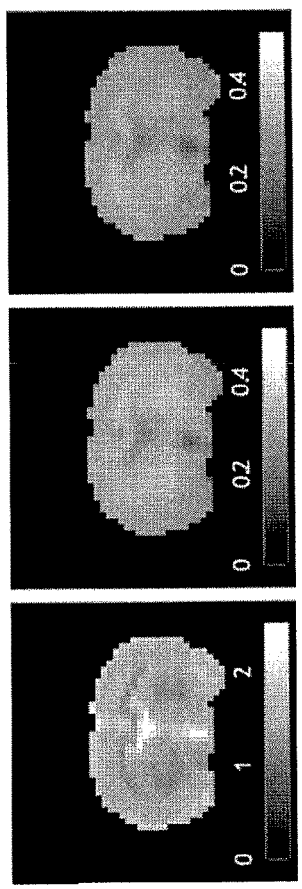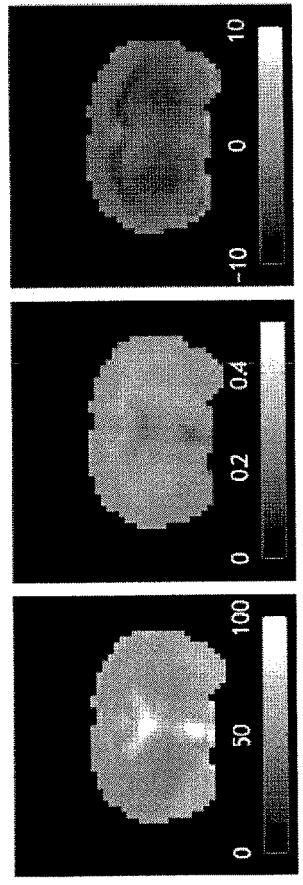

$T_1$ (s)

$T_2$ (ms)

CBF(ml/g.min)

ADC (um2/ms)

$MTR_{asym}$ (%)

$\Delta APTR$ (%)

SYSTEM AND METHOD FOR CORRECTING INTRINSIC HETEROGENEITY IN MAGNETIC RESONANCE IMAGING

CROSS-REFERENCE TO RELATED APPLICATIONS

The application represents the U.S. National Stage of International Application No. PCT/US2015/026303, filed Apr. 17, 2015 which is based on, claims priority to, U.S. Provisional Application Ser. No. 61/981,471 filed Apr. 18, 2014, both of which are incorporated herein by reference for all purposes.

STATEMENT REGARDING FEDERALLY SPONSORED RESEARCH

This invention was made with government support under 1K01EB009771, 1R21NS085574 and 1R01NS083654 awarded by National Institutes of Health. The government has certain rights in the invention.

BACKGROUND

The field of the disclosure is magnetic resonance imaging ("MRI") systems and methods. More particularly, the disclosure relates to systems and methods for improved correction of MR images for intrinsic heterogeneity.

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_t$. A signal is emitted by the excited nuclei or "spins," after the excitation signal $B_1$ is terminated, and this signal may be received and processed to form an image.

In MRI systems, the excited spins induce an oscillating sine wave signal in a receiving coil. The frequency of this signal is near the Larmor frequency, and its initial amplitude, $A_0$, is determined by the magnitude of the transverse magnetic moment $M_t$. The amplitude, A, of the emitted NMR signal decays in an exponential fashion with time, t. The decay constant $1/T^{*}2$ depends on the homogeneity of the magnetic field and on $T_2$, which is referred to as the "spin-spin relaxation" constant, or the "transverse relaxation" constant. The $T_2$ constant is inversely proportional to the exponential rate at which the aligned precession of the spins would dephase after removal of the excitation signal $B_1$ in a perfectly homogeneous field. The practical value of the $T_2$ constant is that tissues have different $T_2$ values and this can be exploited as a means of enhancing the contrast between such tissues.

Another important factor that contributes to the amplitude A of the NMR signal is referred to as the spin-lattice relaxation process that is characterized by the time constant $T_1$. It describes the recovery of the net magnetic moment M to its equilibrium value along the axis of magnetic polarization (z). The $T_1$ time constant is longer than $T_2$, much longer in most substances of medical interest. As with the $T_2$ constant, the difference in $T_1$ between tissues can be exploited to provide image contrast.

Thus, images weighted based on the $T_1$ or $T_2$ time constants can be referred to as relaxation weighted imaging; however, a variety of other contrast mechanisms have also been developed. For example, a so-called diffusion weighted imaging (DWI) pulse sequence uses motion sensitizing magnetic field gradients to obtain images having contrast related to the diffusion of water or other fluid molecules. Specifically, a DWI pulse sequence applies diffusion sensitizing magnetic field gradients in selected directions during the MRI measurement cycle to obtain MR images that have an image contrast related to the diffusion of water or other fluid molecules that occurred during the application of the diffusion gradients. Using these DWI images, an apparent diffusion coefficient (ADC) may be calculated for each voxel location in the reconstructed images.

The particular information sought in given clinical application may dictate a desired contrast mechanism (for example, $T_1$ weighting, $T_2$ weighting, diffusion weighting, perfusion imaging, and the like). For example, DWI and its metric, ADC, have been widely used to evaluate subjects after stroke and guide clinical decisions. In addition to DWI and ADC, another MR diffusion metric has been proposed called diffusion kurtosis imaging (DKI). For example, DKI has been used to study brain disorders, assess cerebral infarction, and assess stroke.

In particular, DKI relies upon the knowledge that water diffusion in biological tissues is non-Gaussian and; thus, DKI extends conventional diffusion tensor imaging (DTI) by estimating the non-Gaussianity of the water diffusion probability distribution as reflected by data acquired from a subject. To this end, the "kurtosis" is a dimensionless means through which one can quantify the non-Gaussianity of data. When considering a given set of data, a positive kurtosis indicates that the data is more strongly peaked and has lighter tails than a set of data that matched a Gaussian distribution.

Qualitatively, a large diffusional kurtosis suggests a high degree of diffusional heterogeneity and microstructural complexity. Unfortunately, since DKI is heterogeneous in normal brain, it can be difficult to quantify kurtosis abnormality. As such, when attempting to use DKI for particular clinical applications, such as stroke evaluation, it can be difficult to precisely delineate stroke-induced lesion using DKI.

Thus, it would be desirable to have a system and method for providing improved clinical information using contrast mechanisms, such as DKI or others like chemical exchange saturation transfer (CEST), magnetization transfer (MT), amide proton transfer (APT), images against intrinsic heterogeneity.

SUMMARY

In one example, the present disclosure overcomes the aforementioned drawbacks by providing a system and method for correcting for intrinsic heterogeneity and improving contrast, such as to yield improved lesion conspicuity. In particular, baseline MR data may be used to establish baseline correlation parameters that may include, for example, $R_1$ (i.e., $1/T_1$), $R_2$ (i.e., $1/T_2$) and magnetization transfer ratio (MTR) that can be used to create baseline-normalized kurtosis data. The normalized kurtosis (MK') MRI effectively reduces the intrinsic kurtosis heterogeneity. The present disclosure provides various clinically-useful reports that can be created using the relaxation-normalized kurtosis (MK') MRI data, including automated tissue segmentation of the kurtosis lesion for use in, for example, clinical applications such as analyzing acute ischemic stroke.

In accordance with one aspect of the disclosure, a magnetic resonance imaging (MRI) system is disclosed that includes a magnet system configured to generate a polarizing magnetic field about at least a region of interest (ROI) of a subject arranged in the MRI system, the ROI including tissue believed to be pathological tissue. The MRI system also includes a plurality of gradient coils configured to apply a gradient field with respect to the polarizing magnetic field and a radio frequency (RF) system configured to apply RF excitation fields to the subject and acquire MR image data therefrom. The MRI system further includes a computer programmed to control the plurality of gradient coils and the RF system to acquire diffusion kurtosis imaging (DKI) data from the ROI and determine baseline correlation parameters from baseline MR data. The computer is further programmed to generate relaxation-normalized kurtosis data using the baseline correlation parameters to correct the DKI data at least for relaxation variations affecting kurtosis in the DKI data and generate a report using the relaxation-normalized kurtosis data.

In accordance with another aspect of the present disclosure, a method is provided for acquiring images of a region of interest (ROI) of a subject using a magnetic resonance imaging system. The method includes acquiring pathological diffusion kurtosis imaging (DKI) data from tissue in the ROI believed to be pathological tissue, acquiring baseline DKI data for tissue believed to not be pathological tissue, and determining correlation parameters from baseline DKI data. The method further includes generating corrected kurtosis data using the baseline correlation parameters by reducing intrinsic heterogeneity in the pathological DKI data and generating a report using the corrected kurtosis data.

In accordance with yet another aspect of the present disclosure, a method is provided for acquiring images of a region of interest (ROI) of a subject using a magnetic resonance imaging system. The method includes acquiring data from tissue in the ROI believed to be pathological tissue, acquiring baseline data from tissue in the subject believed to not be pathological tissue, and determining correlation parameters from baseline data. The method also includes generating corrected data using the baseline correlation parameters such that the corrected data is processed at least for intrinsic heterogeneity, and generating a report using the corrected data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 8A is an image of a $T_1$ map of a representative normal rat.

FIG. 8B is an image showing elevated intensity in $T_1$ due to elevated water content.

FIG. 8C is an image showing ventricle MTR map at a labile frequency (3.5 ppm).

FIG. 8D is an image showing ventricle MTR map at a reference frequency (−3.5 ppm).

FIG. 8E is an image showing the mean MTR map.

FIG. 8F is an image showing pH-sensitive $MTR_{asym}$ map.

FIG. 12A is an image showing hypoperfusion in the ischemic stroke.

FIG. 12B is an image showing pH lesion using the proposed APT MRI.

FIG. 12C is an image showing diffusion lesion in the ischemic stroke.

FIG. 12D is a graph comparing acute stroke perfusion, pH and diffusion lesion volumes in accordance with the present disclosure.

DETAILED DESCRIPTION

Figure 1:
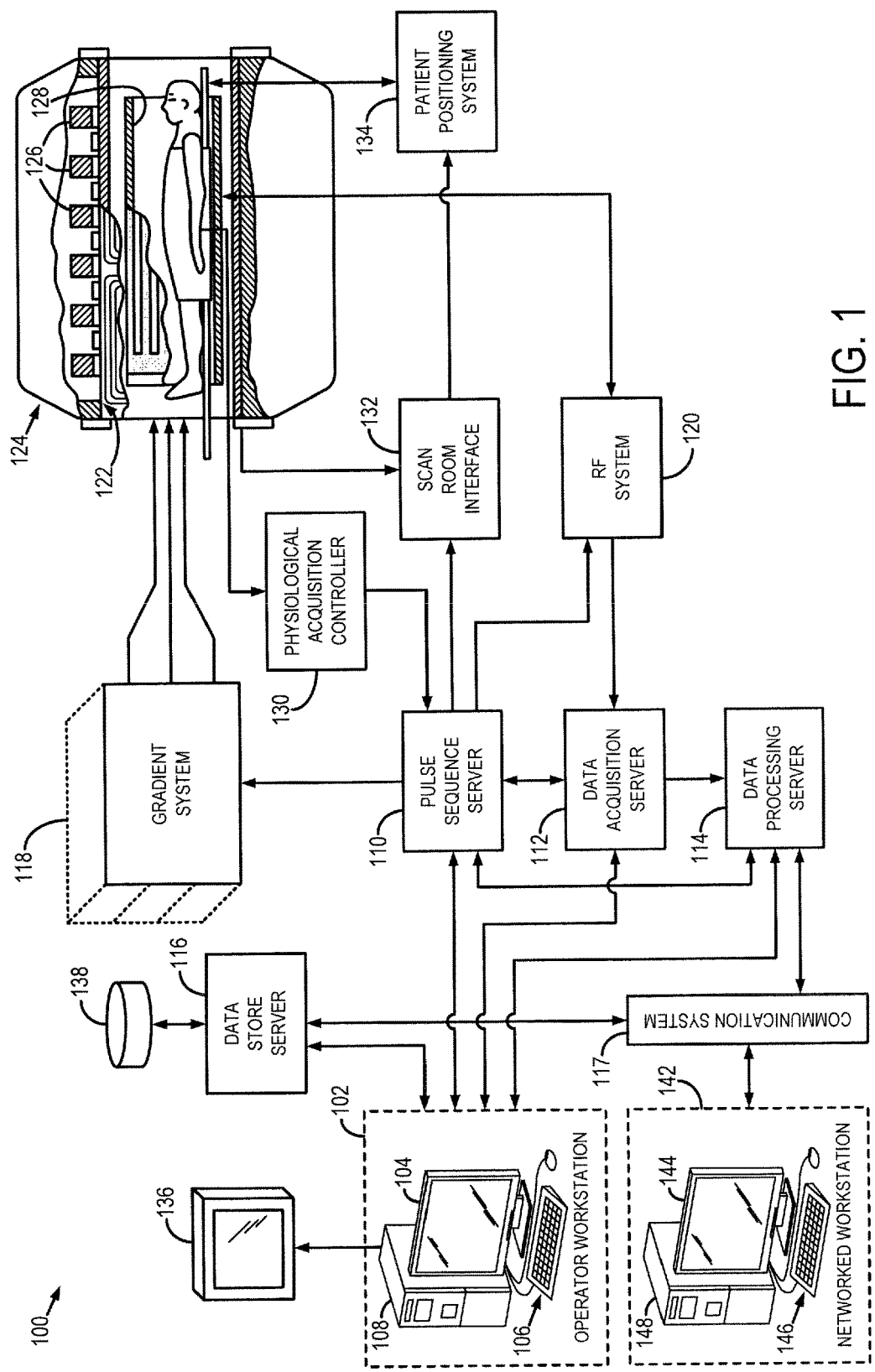
FIG. 1 is a block diagram of an MRI system that employs the present disclosure.
Figures 2A, 2B, 2C, 2D, 2E:
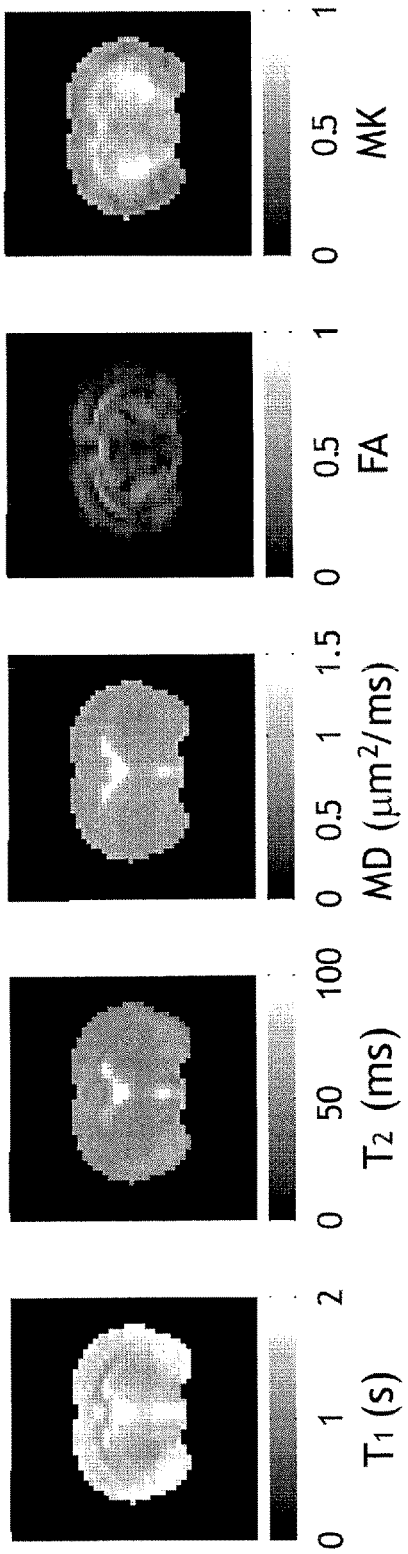
FIG. 2A is an image showing multi-parametric $T_1$ acquired from a representative normal adult Wistar rat during a study conducted in accordance with the present disclosure.
FIG. 2B is an image showing $T_2$ acquired from a representative normal adult Wistar rat during a study conducted in accordance with the present disclosure.
FIG. 2C is an image showing mean diffusivity (MD) acquired from a representative normal adult Wistar rat during a study conducted in accordance with the present disclosure.
FIG. 2D is an image showing fractional anisotropy (FA) acquired from a representative normal adult Wistar rat during a study conducted in accordance with the present disclosure.
FIG. 2E an image showing mean kurtosis (MK) acquired from a representative normal adult Wistar rat during a study conducted in accordance with the present disclosure.
Figure 3A:
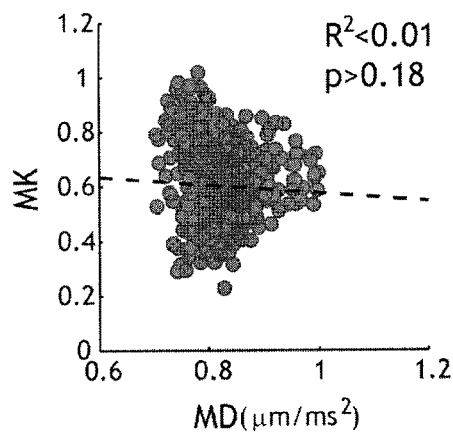
FIG. 3A is a graph created using a univariate regression between MK and multi-parametric MRI indexes and showing MK with MD.
Figure 3B:
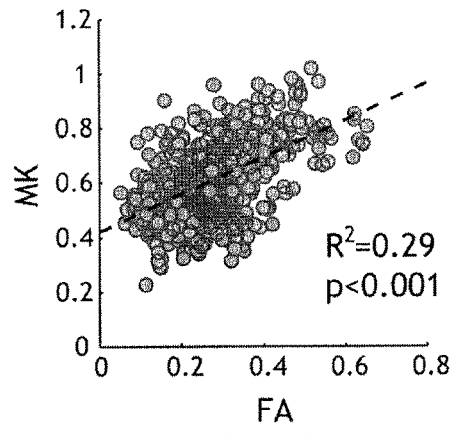
FIG. 3B is a graph created using a univariate regression between MK and multi-parametric MRI indexes and showing MK with FA.
Figure 3C:
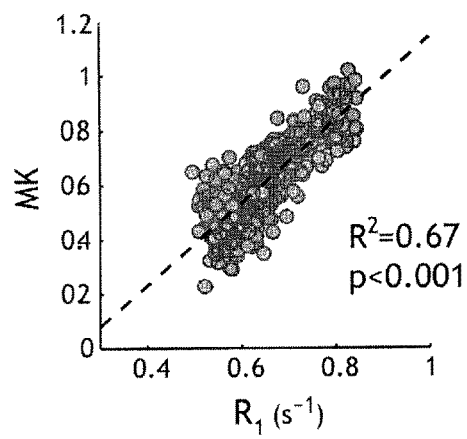
FIG. 3C is a graph created using a univariate regression between MK and multi-parametric MRI indexes and showing MK with $R_1$.
Figure 3D:
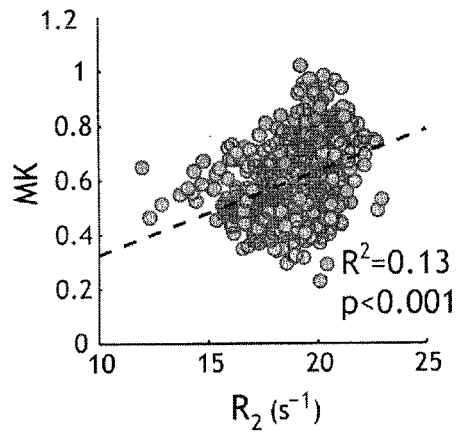
FIG. 3D is a graph created using a univariate regression between MK and multi-parametric MRI indexes and showing MK with $R_2$.

Referring particularly now to FIG. 1, an example of a magnetic resonance imaging (MRI) system 100 is illustrated. The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients and used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the quadrature components of the received magnetic resonance signal. The magnitude of the received magnetic resonance signal may, therefore, be determined at any sampled point by the square root of the sum of the squares of the and components:

$$M=\sqrt{I^2+Q^2} \qquad \text{Eqn. (1)};$$

and the phase of the received magnetic resonance signal may also be determined according to the following relationship:

$$\varphi = \tan^{-1}\left(\frac{Q}{I}\right). \qquad \text{Eqn. (2)}$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than passing the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

The above-described MRI system 100 may be used to perform a variety of imaging processes including diffusion-weighted imaging (DWI) and diffusion-kurtosis imaging (DKI). DWI can be used to detect severely damaged ischemic tissue that is likely to infarct and has been widely used in stroke imaging. However, tissue damage within DWI deficit is heterogeneous, which may partially recover with prompt treatment. There have been no well-established techniques capable of stratifying heterogeneously damaged DWI lesion. Diffusion kurtosis imaging is an emerging MRI technique that measures the degree of the non-Gaussian water diffusion and is sensitive to microscopic structural changes. Indeed, diffusion kurtosis imaging has been shown capable of detecting microstructural cerebral tissue changes in aging brains, acute stroke, trauma, and tumor. However, while DKI has been shown to stratify heterogeneous DWI lesions, improving characterization of tissue injury, because DKI is heterogeneous in normal brain, it can be difficult to precisely delineate stroke-induced DKI lesion. Thus, quantification or automated DKI lesion delineation has not previously been possible. However, as will be described, the present disclosure provides a system and method that uses $T_1$ image or magnetization transfer (MT) image to correct for intrinsic DKI heterogeneity to significantly improves DKI lesion conspicuity.

Studies of transient ischemic stroke have demonstrated that mean kurtosis (MK) lesion captures the irreversibly damaged ischemic core, and hence, delineates the standard DWI lesion for improved stratification of graded ischemic tissue injury. However, unlike the relatively homogeneous trace diffusion image, the complexity of cerebral structure and composition leads to a heterogeneous MK map, in which the specificity of kurtosis abnormality to ischemia is somewhat compromised. A means to minimize the intrinsic cerebral tissue MK variation would thus enhance the conspicuity of the ischemic kurtosis lesion, to in turn facilitate the practical use of kurtosis MRI in the setting of acute stroke.

The present disclosure recognizes a correlation between relaxation with kurtosis, which suggests that the intrinsic kurtosis heterogeneity is largely attributable to myelin-induced microstructure. A linear correlation between $R_1$ ($1/T_1$) and MT was explored and it was discovered that $R_1$ has the strongest association with kurtosis. However, as will be explained, multiple parameters and a multiple-linear regression can be used for improved correction.

In particular, a study was conducted to investigate the pixelwise correlation between cerebral mean kurtosis (MK) with multi-parametric MRI indexes including mean diffusivity (MD), fractional anisotropy (FA), and relaxation ($R_1$, $R_2$) rates. The results showed significant correlation between MK and $R_1$, $R_2$ and FA, with $R_1$ showing the strongest correlation. Because diffusion rate and fraction anisotropy may change substantially during acute stroke while the change in relaxation measurements is relatively small, the study showed that relaxation-normalized kurtosis imaging could significantly mitigate the intrinsic kurtosis heterogeneity. Further it was demonstrated that by reducing this intrinsic kurtosis variation in accordance with the present disclosure using a modified kurtosis MRI technique in accordance with the present disclosure, the definition of the ischemic kurtosis lesion was enhanced. Thus, the present disclosure provides a relaxation-normalized kurtosis MRI technique that is effective for use in a variety of clinical applications including for improved characterization of ischemic kurtosis lesion, which is an important metric for evaluating the diagnostic value of diffusion kurtosis MRI (DKI) during acute ischemic stroke.

Study

Specifically, in the above-described study, adult male Wistar rats (Charles River Laboratory, Wilmington, Mass.) were anesthetized throughout the experiments with 1.5-2.0% isoflurane in air. Partial pressure of oxygen in the blood and heart rate were monitored online (Nonin Pulse Oximeter 8600, Plymouth, Minn.). Animal body temperature was maintained by a circulating warm water jacket positioned around the torso. We imaged seven normal rats (N=7) and fifteen rats with middle cerebral artery occlusion (MCAO), a standard experimental stroke model (N=15). Briefly, MCAO was induced by inserting a 4-0 silicon-coated nylon suture into the lumen of the internal carotid artery, and then advancing it to block the origin of the middle cerebral artery; this procedure has been described in detail in previously-published work by the inventors, Sun P Z, Wang E F, Cheung J S. Imaging acute ischemic tissue acidosis with pH-sensitive endogenous amide proton transfer (APT) MRI—Correction of tissue relaxation and concomitant RF irradiation effects toward mapping quantitative cerebral tissue pH. Neuroimage 2012; 60(1):1-6, which is incorporated herein by reference in its entirety. The MCAO procedure failed in two animals, which we hence excluded from further study.

MRI data was acquired using a 4.7 Tesla small-bore MRI scanner (Bruker Biospec, Billerica, Mass.). Multi-slice MRI (5 slices, slice thickness/gap=1.8/0.2 mm, field of view=20× 20 mm$^2$, acquisition matrix=48×48) was acquired with single-shot echo-planar imaging (EPI) (receiver bandwidth=225 kHz), with the central slice positioned 2 mm posterior to bregma. Diffusion-weighted MRI was acquired with spin echo (SE) EPI with eight b-values of 250, 500, 750, 1000, 1500, 2000 and 2500 s/mm$^2$ (gradient pulse duration/diffusion time ($\delta/\Delta$)=6/20 ms, TR/TE=2500/40.5 ms, NAE=4) along six directions. In addition, $T_1$-weighted images were acquired using an inversion recovery sequence, with seven inversion delays ranging from 250 ms to 3000 ms (TR/TE=6500/14.8 ms, NAE=4); $T_2$-weighted SE images were obtained with two TEs of 30 and 100 ms (TR=3250 ms, NAE=16).

Images were analyzed in MATLAB (MathWorks, Natick, Mass.). Apparent diffusion ($D_{app}$) and kurtosis coefficients ($K_{app}$) were calculated per pixel along each diffusion direction by least-square fitting the DWI signals non-linearly to $S(b)=S(0) \exp(-bD_{app}+\frac{1}{6}b^2 D_{app}^2 K_{app})$, where $S(b)$ is the DWI signal at a given b-value and $S(0)$ is the signal without diffusion weighting. Mean diffusion coefficient (MD) and kurtosis coefficient (MK) were calculated as the average of $D_{app}$ and $K_{app}$ along each diffusion direction, respectively. In addition, parametric $T_1$ and $T_2$ maps were obtained using least-squares fitting of the signal intensities as functions of inversion time ($I=I_0|1-(1-\eta)e^{-TI/T_1}|$), where $\eta$ is the inversion efficiency, and echo time ($I=I_0 e^{-TE/T_2}$), respectively. Results were expressed as mean±standard deviation (S.D.). The association between MK and relaxation, MD and FA were evaluated with univariate and multiple regressions, and p-values of less than 0.05 were considered statistically significant.

Results

Referring now to FIGS. 2A through 2E, parametric brain $T_1$, $T_2$, MD, FA, and MK MRI images, respectively, are provided that were acquired from a representative adult normal Wistar rat using the above-described process. Because cerebral spinal fluid (CSF) has significantly higher water content and diffusivity, the ventricle region appears hyperintensive in the $T_1$, $T_2$ and MD maps, while hypointensive in the FA and MK maps due to less anisotropic/restricted diffusion of CSF. Notably, whereas the contrast between striatum and corpus callosum regions and cortex was relatively small in the $T_2$ and MD maps, it became very distinct in the $T_1$, FA and MK maps. This suggested that kurtosis, a measure of non-Gaussian diffusion, could be associated with diffusion fraction anisotropy, an index of microstructure complexity and longitudinal relaxation time, which has been shown to be associated with underlying semisolid macromolecules.

The relationship between MK and multivariate MRI indexes was evaluated using Pearson's correlation with a Student's t distribution, excluding ventricle regions using a diffusion threshold-based mask (MD<1.0 μm$^2$/ms). As FIGS. 3A through 3D show, there was comparatively little correlation between MK and MD ($R^2$<0.01, P>0.18), suggesting that MK is indeed different from the standard and widely used MD index. The per-pixel analysis showed significant correlation between MK and FA ($R^2$=0.29, P<0.001, FIG. 2 b), MK and $R_1$ ($R^2$=0.67, P<0.001, FIG. 2 c), and MK and $R_2$ ($R^2$=0.13, P<0.001, FIG. 2 d). Notably, the correlation between MK and $R_1$ was significantly higher than that of MD, FA and $R_2$ (P<0.001). Because MD and FA may change substantially during acute stroke, the univariate regression of MK and $R_1$ was compared versus multiple regression of MK with $R_1$ and $R_2$. It was found that the coefficient of determination (i.e., $R^2$) was 0.60±0.09 (MK and $R_1$, P<0.001) and 0.61±0.09 (MK, $R_1$ and $R_2$, P<0.01). There was no significant difference between the $R^2$ obtained by univariate regression of MK and $R_1$ and that determined by multiple regression of MK, $R_1$ and $R_2$ (Two-sample t-test, P>0.80).

In a comparison of a conventional MK map and a relaxation-scaled MK map in accordance with the present disclosure, the conventional MK map showed hyperintensity in regions of the striatum and corpus callosum, indicating complex local microstructure. An estimated MK map ($MK_{est}$) was created using the linear regression coefficients determined from MK and $R_1$, per pixel from the same slice and animal ($MK_{est}$=1.51*$R_1$−0.37). Also, a relaxation-normalized MK map, denoted "MK'" and equal to MK/$MK_{est}$, was created, which was significantly more homogeneous than the conventional, raw MK map. The coefficient of variation (COV, i.e., S.D./mean) was 22.4 and 14.0 for the conventional MK and relaxation-normalized MK maps, respectively. This represented a relative COV decrease of 37.5 percent, confirming that the relaxation-normalized MK (MK') map in accordance with the present disclosure can reasonably account for a significant portion of the MK heterogeneity in the intact brain.

Figure 4:
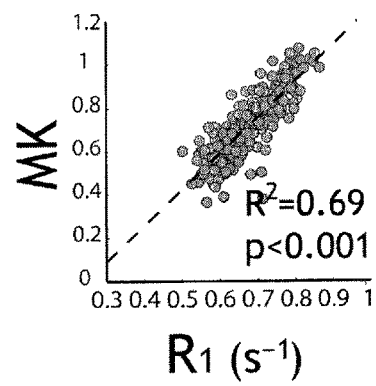
FIG. 4 is a graph showing univariate regression analysis of $R_1$ and MK in the contralateral normal brain.

The relaxation-normalized MK (MK') MRI in accordance with the present disclosure was tested with respect to stroke animals within 2 hrs after MCAO. Both the $R_1$ and MK maps in the MCAO group showed hyperintensity in regions of the striatum and corpus callosum, similar to what was observed in normal brains. Importantly, the ischemia-induced MK abnormality overlapped with regions of intrinsic kurtosis hyperintensity, particularly in the ipsilateral internal capsule, resulting in grossly overestimated kurtosis elevation. Using the contralateral normal brain as the reference, FIG. 4 shows that MK correlates with $R_1$ ($R^2$=0.69, P<0.001), also similar to the findings in normal brains. The linear regression between MK and $R_1$ was determined from the contralateral normal regions, and the MK map was estimated ($MK_{est}$) from the $R_1$ map per pixel. In the contralateral brain, MK and relaxation-normalized MK map (MK') were 0.69±0.16 and 1.00±0.14, respectively. This represented a relative COV decrease of 39.6 percent, a decrease similar to that seen in normal brains. As MK' reasonably normalized regional MK variability, it may be used to facilitate tissue segmentation for defining ischemic kurtosis lesion. To this end, a threshold-based algorithm was tested to identify kurtosis lesion with MK' of more than two standard deviations from the mean, calculated from the contralateral normal brain, which reasonably defined the ischemic kurtosis lesion.

Figure 5A:
FIG. 5A is an image set showing ischemic tissue segmentation using a segmentation process in accordance with the present disclosure leveraging relaxation-normalized kurtosis MRI to illustrate MD lesion.
Figure 5B:
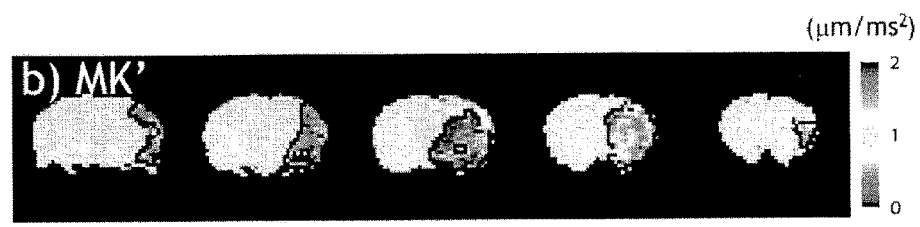
FIG. 5B is an image set showing ischemic tissue segmentation using a segmentation process in accordance with the present disclosure leveraging relaxation-normalized kurtosis MRI to illustrate MK' lesion.
Figure 6:
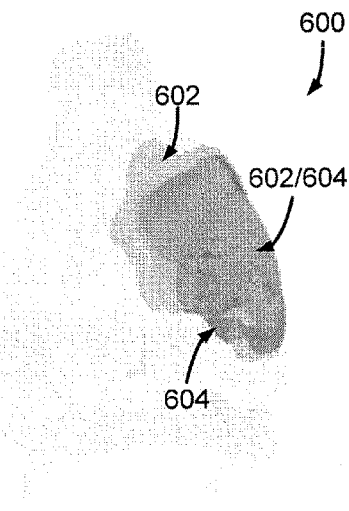
FIG. 6 is a representation of a three-dimensional (3D) overlay of MD and MK' lesions segmented as illustrated with respect to FIGS. 5A and 5B in accordance with the present disclosure.

Using the proposed relaxation-normalized kurtosis MRI, diffusion and kurtosis lesions were compared during acute ischemic stroke. For example, FIG. 5A shows a representative acute stroke animal with diffusion and FIG. 5B shows the intrinsic heterogeneity corrected kurtosis map. In FIGS. 5A and 5B, lesions were defined using a threshold-based algorithm that used two standard deviations from the mean as the threshold. Referring to FIG. 6, the lesions were superimposed on a scout scan 600, in which a diffusion (MD) lesions 602 and a relaxation-normalized kurtosis (MK') lesion 604 are shown. FIG. 5 shows that the MK' lesion 604 was within the MD lesion 602, with diffusion/kurtosis lesion mismatch in anterior and superior portions of the ischemic lesion.

Figure 7:
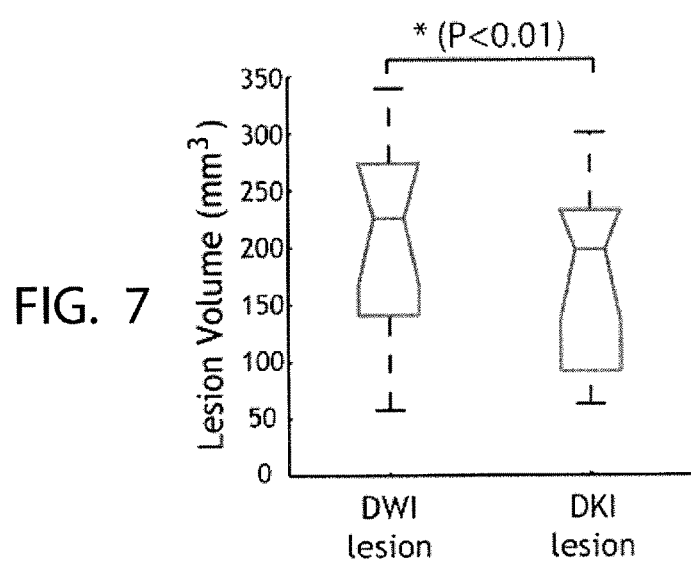
FIG. 7 is a graph comparing acute stroke diffusion and kurtosis lesion volumes in accordance with the present disclosure.

FIG. 7, which compares the diffusion and kurtosis lesion volumes in all fifteen stroke animals utilized in the above-described study, shows the median diffusion and kurtosis lesion volumes were 226 mm$^3$ and 198 mm$^3$, respectively. Using a one-tailed paired t-test ($P<0.01$) we found that the kurtosis lesion volume (172±78 mm$^3$) was significantly less than that of diffusion (206±93 mm$^3$). Moreover, MD was 0.64±0.05 and 0.64±0.04 in the MD and MK' lesions, respectively, and there was no statistically significant difference ($P=0.61$). Importantly, MK' was significantly different between MD and MK' lesions (1.58±0.10 vs. 1.70±0.11, $P<0.001$).

The above-described study showed significant correlation between the mean kurtosis and longitudinal relaxation measurements, and demonstrated that relaxation-normalized kurtosis MRI reduces the intrinsic mean kurtosis heterogeneity in brain. Because change in the longitudinal relaxation rate during acute ischemic stroke is relatively small, we demonstrated that the modified kurtosis MRI technique enables automated tissue segmentation to define the acute ischemic kurtosis lesion. The results also showed significant mismatch between the diffusion and kurtosis lesion volumes, indicating that kurtosis provides a promising new index for stratifying the heterogeneous ischemic DWI deficits. We also showed there was no statistically significant difference in mean diffusivity between diffusion and kurtosis lesions ($P=0.61$), consistent with prior studies that showed the DWI lesion cannot be reliably segmented based on the severity of diffusion decrease. Importantly, we found that kurtosis was significantly different between the kurtosis and diffusion lesions, suggesting that the kurtosis index complements the standard stroke diffusion MRI method, and serves as a promising means by which to delineate the heterogeneous diffusion stroke lesion. That is, the results demonstrate that relaxation-normalized kurtosis (MK') MRI effectively reduced the intrinsic kurtosis heterogeneity, enabling automated tissue segmentation of the kurtosis lesion, for example, in clinical applications such as acute ischemic stroke.

There is significant diffusion and kurtosis lesion mismatch during acute stroke, and that the diffusion lesion without kurtosis abnormality responds favorably to early reperfusion while kurtosis lesion shows poor response. Notably, the mechanism of MK contrast in acute stroke is very complex. The diffusion lesion in the diffusion/kurtosis mismatch area may be largely attributed to the net shift of extracellular water into the restricted intracellular compartment associated with the dysfunction of trans-membrane ion channels. In contrast, simultaneous diffusion and kurtosis changes likely indicate pronounced intracellular tortuosity and viscosity elevation, markers of irreversible cell damage. The relaxation-scaled kurtosis index enables automated tissue segmentation of otherwise heterogeneous kurtosis MRI to facilitate ongoing investigation of the diagnostic value of kurtosis MRI in acute stroke and potential imaging-guided stroke therapies.

The results of the study have also demonstrated significant correlation between kurtosis and diffusion fraction anisotropy ($P<0.001$). As such, it is likely that macromolecules, such as myelin may affect multiple brain MRI indexes, which may further explain the correlation among these measurements. Moreover, the study showed that the correlation between longitudinal relaxation and kurtosis measurements accounted for approximately 60 percent of kurtosis heterogeneity in the intact brain. Other MRI indexes, such as magnetization transfer (MT) MRI, may be used to further enhance the correlation. Thus, the above-described process may be part of multi-parametric MRI acquisition that extends beyond $T_1$ and kurtosis. In addition, whereas the above study used a ratio-metric normalization approach, intrinsic kurtosis heterogeneity may also be mitigated by using algorithms to evaluate variables, such as the difference between the acquired and estimated kurtosis maps. The study investigated parametric maps for correcting kurtosis heterogeneity. Non-parametric images such as $T_1$-weighted, $T_2$-weighted, and MT-weighted images may be applied to correct the intrinsic heterogeneity in kurtosis and CEST maps. Furthermore, the above-described techniques may also be combined with techniques such as fingerprinting MRI and fast kurtosis acquisition schemes to further shorten scan time, facilitating their adoption in the clinic.

Figure 13:
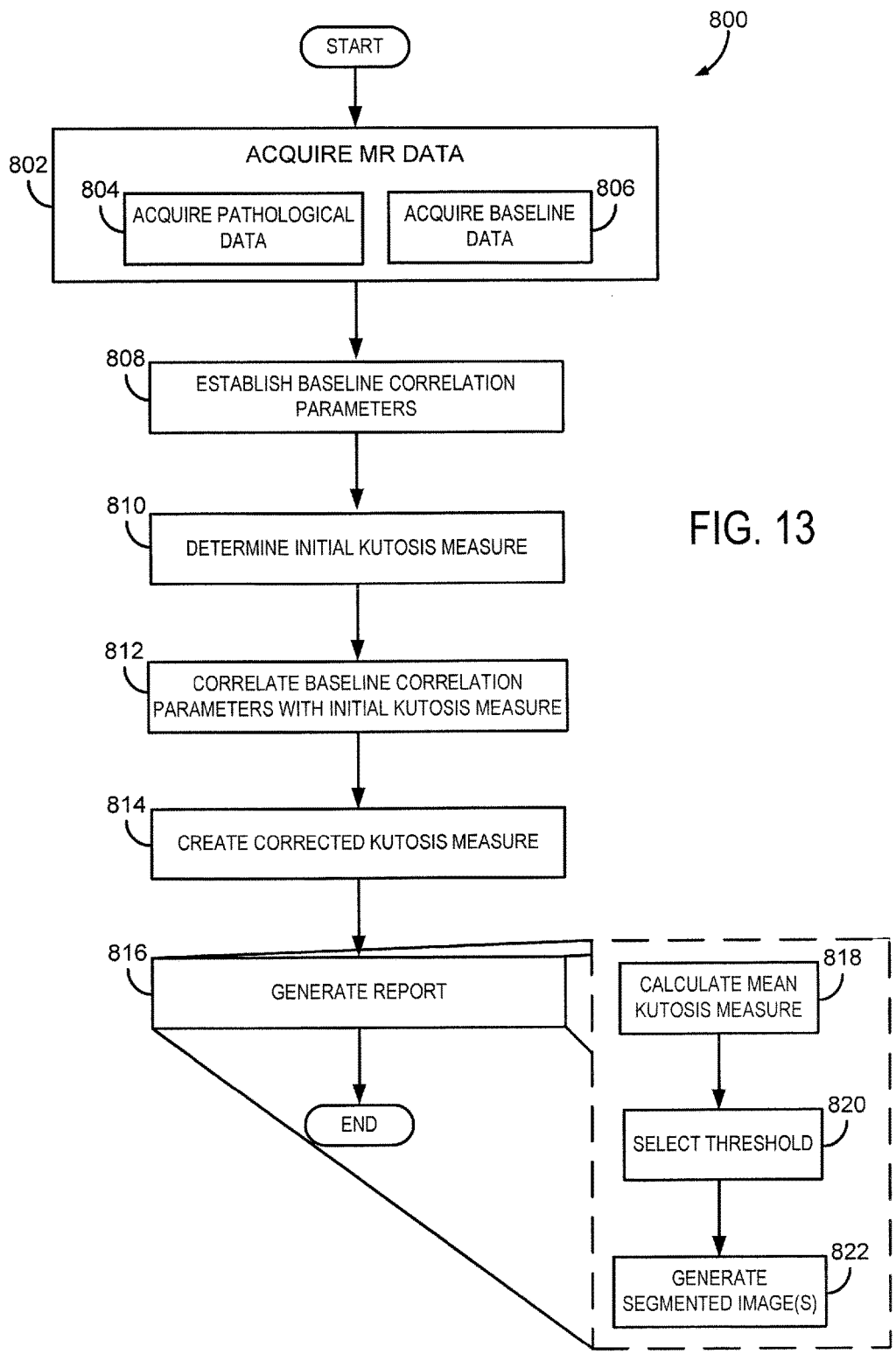
FIG. 13 is a flow chart of a process in accordance with the present disclosure.

The above-described systems, methods, and techniques may be applied to general imaging applications, for example, using the MRI system of FIG. 1. In particular, referring to FIG. 13, a process 800 is illustrated for performing DKI with correlation to additional information to provide an improved measure of DKI that compensates for heterogeneity similarities between normal and pathological tissue. As such, the DKI data may be corrected for intrinsic DKI heterogeneity and, if desired, improved segmentation may be performed based thereon. The process 800 beings at process block 802 with the acquisition of MR data. Specifically, process block 802 includes the acquisition pathological MR data 804 from a subject. In particular, the acquired pathological MR data includes diffusion data consistent with DKI and at least one other contrast mechanism. For example, the other contrast mechanism may be $T_1$ or MT data or the like. Also, process block 802, includes the acquisition of baseline MR data 806. Notably, the acquisition of pathological data 804 and baseline data 806 may occur simultaneously or may be serially performed. For example, when imaging the brain for stroke analysis, the pathological MR data may be acquired from a hemisphere of the brain suspected of suffering the stroke, whereas the baseline data may be acquired from a hemisphere of the brain believed to be normal. To this end, the pathological and baseline MR data may be acquired in a single acquisition. Alternatively, the pathological and baseline MR data may be acquired in separate acquisitions or even separate studies. For example, the baseline data may be acquired during a study performed at a time known to precede the suspected stroke. In this case, the data may be acquired from the same hemisphere.

At 808, the baseline MR data is used to establish baseline correlation parameters that may include, for example, $R_1$, $R_2$, FA, magnetization transfer ratio (MTR), and the like. At process block 810, an initial determination of kurtosis is made using the pathological MR data. As will be recognized by one of ordinary skill in the art, for example, process block 808 and 810 may be performed in different orders. In any case, thereafter at process block 812, the baseline correlation parameters are correlated with initial determination of kurtosis. That is, as described above, intrinsic kurtosis heterogeneity can be corrected using parametric and multi-parametric MRI indexes.

At process block 814, a corrected kurtosis measure is created. That is, the baseline kurtosis can be used to correct or adjust the initial determination of kurtosis. For example, the coefficients from the correlation parameters can be used to create a relaxation-normalized kurtosis or MK'. Also, other calculations can be performed. For example, a ratio or difference of the baseline kurtosis and the initial determination of kurtosis can be created.

At process block 816, a report is generated, which may take a variety of forms. For example, the corrected kurtosis measure may be reported or the relaxation-normalized kurtosis map displayed. Furthermore, the corrected or relaxation-normalized kurtosis or MK' may be used to facilitate tissue segmentation, for example, for defining ischemic kurtosis lesion. To this end, one example of a process for generating a report at process block 816 may include the use of a threshold-based algorithm to identify kurtosis lesion with MK'. For example, in the clinical application of segmenting brain lesions, the process for generating a report at process block 816 may optionally include calculating a mean kurtosis measure of the contralateral normal brain using the baseline kurtosis measure, at process block 818. At process block 820, a threshold is selected. The threshold may be a standard deviation threshold, for example, a threshold of more than two standard deviations from the mean calculated from the contralateral normal brain. That is, as previously described, the present disclosure demonstrated that relaxation-normalized kurtosis (MK') MRI effectively reduced the intrinsic kurtosis heterogeneity and automated tissue segmentation of the kurtosis lesion, for example, in clinical applications such as acute ischemic stroke, can be used to exploit this achievement. At process block 822, the threshold is applied to determine the ischemic kurtosis lesion and generate a segmented image based thereon to be included in the report generated at process block 816.

The present disclosure can be applied for correcting images such as chemical exchange saturation transfer (CEST) and magnetization transfer (MT) MRI. The above-described approach has been demonstrated to apply in pH-sensitive endogenous amide proton transfer (APT), a specific form of endogenous CEST MRI. The intrinsic heterogeneity corrected APT MRI suppresses white/gray matter contrast in the normal regions, permitting delineation of acidic tissue with a threshold-based algorithm.

One particular challenge of pH-sensitive APT image analysis in acute stroke imaging is that in vivo APT-weighted map (i.e., $MTR_{asym}$) is heterogeneous. Specifically, brain corpus callosum and striatum appear substantially hypointense when compared to that of cortex. Because intrinsic pH difference between brain white matter (WM) and grey matter (GM) tissue has been found to be less than 0.05, the heterogeneity observed in $MTR_{asym}$ map is likely attributable to the difference in the underlying macromolecular composition and microstructure. Because of the different baseline between normal brain WM and GM, acidic ischemic tissue identified from pH-weighted MRI has to be manually outlined for different tissue types based on the contralateral normal region following acute ischemia stroke. This technical difficulty tremendously hinders the adoption of pH-weighted MRI in the acute stroke setting where reliable and fast tissue classification is necessary to define ischemic penumbra for guiding stroke treatment. There is demonstrable need to develop a simplified yet reproducible in vivo APT image analysis approach to minimize $MTR_{asym}$ heterogeneity and ultimately facilities ischemic tissue.

The intrinsic MTR asymmetry shift (i.e., $MTR'_{asym}$) approximately scales with $R_{1w}$, which allows tissue pH estimation from pH-weighted MRI. The present disclosure evaluated the $R_{1w}$-scaled APT (RAPT) MRI in an animal model of acute ischemic stroke and tested whether a threshold-based tissue segmentation algorithm can demarcate acidic tissue. This showed that RAPT MRI significantly decreased variation in pH-weighted APT MRI image. Thus, threshold-based image analysis algorithms, such as described above, can be used to delineate acidic lesion in addition to perfusion and diffusion MRI lesions. Thus, the present disclosure provides a $R_{1w}$-scaled APT map that significantly reduced apparent heterogeneity in the widely used $MTR_{asym}$ map, enabling ischemic tissue segmentation.

Specifically, the in vivo pH-weighted APT (i.e. CEST) effect can be described by an empirical solution:

$$MTR_{asym} = APTR + MTR'_{asym} \quad (3)$$
$$= \frac{f_s \cdot k_{sw}}{R_{1w} + f_s \cdot k_{sw}} \cdot \alpha \cdot (1-\sigma) + MTR'_{asym};$$

where $MTR_{asym}$ is the experimentally measured MTR asymmetry, which includes contributions from pH-sensitive APT ratio (APTR) and intrinsic MTR asymmetry shift ($MTR'_{asym}$). In addition, $\alpha$ is the labeling coefficient and $\sigma$ is the spillover factor; $k_{sw}$ is pH-dependent amide proton exchange rate, $f_s$ is the labile amide proton concentration with respect to bulk water, and $R_{1w}$ is the bulk water longitudinal relaxation rate. Because the labile amide proton ratio with respect to bulk water is about 1:1000 and the typical amide proton exchange rate is about 30 s$^{-1}$, $f_r \cdot k_{sw} \ll R_{1w}$. Hence, equation 3 can be revised:

$$MTR_{asym} \approx \frac{f_s \cdot k_{sw}}{R_{1w}} \cdot \alpha \cdot (1-\sigma) + MTR'_{asym}. \quad (4)$$

In addition, for moderate RF power levels, the experimental factor shows little dependence for $T_{1w}$ and $T_{2w}$. Hence, $R_{1w}$ scaled APTR effect (i.e. RAPTR=$R_{1w} \cdot MTR_{asym}$) can be shown to be:

$$RAPTR = f_s \cdot k_{sw} \cdot \alpha \cdot (1-\sigma) + MTR'_{asym} \cdot R_{1w} \quad (5)$$
$$= C_0 + C_1 \cdot R_{1w}.$$

During acute ischemic stroke, because the change in relaxation time, NOE and MT effects are relatively small, the ischemia-induced change in RAPT MRI can be derived based on the difference of the experimentally measured RAPTR and that estimated from the linear regression of equation 5. If the intrinsic non-pH sensitive $MTR'_{asym}$ can be estimated and compensated from RAPT MRI, the conspicuity of acidic lesion identified using pH-weighted APT MRI could be significantly enhanced. The correlation coefficients (i.e $C_0$ and $C_1$) can be determined from the contralateral normal brain. Specifically, ischemia-specific change in RAPT MRI can be calculated as:

$$\Delta RAPTR = RAPTR|_{measured} - RAPTR|_{estimated} \quad (6)$$
$$= R_{1w} \cdot MTR_{asym} - (C_0 + C_1 \cdot R_{1w}).$$

Parametric $T_1$, $T_2$ and apparent diffusion coefficient (ADC) maps using least-squares mono-exponential fitting of the signal intensities as functions of inversion time ($I=I_0\lfloor 1-(1-\eta)e^{-TI/T_1}\rfloor$), where $\eta$ is the inversion efficiency, echo time ($I=I_0 e^{-TE/T_2}$), and diffusion b-value ($I=I_0 e^{-b \cdot ADC}$), respectively. Cerebral blood flow (CBF) was computed as $$CBF = \frac{\lambda(I_{ref} - I_{tag})}{2\alpha \cdot I_{ref}} \cdot \frac{e^{w/T_1}}{T_1},$$

where $I_{tag}$ is the label image, $I_{ref}$ is the reference image, $\lambda$ is the brain-blood partition coefficient for water (0.9 mL/g), $\alpha$ is the degree of inversion with transient time correction (0.63), and w is the post-labeling delay.

Thus, the above-described systems and methods can be used to correct for the intrinsic heterogeneity in APT Images in a manner similar to that described above with respect to DKI. For example, $T_1$, an average of reference and label signals, and/or their combinations can be used to correct the APT images.

Turning now to FIGS. 8A-8F, a series of images are provided that shows multi-parametric MRI of a rat. In FIG. 8A, the images shows that the representative normal rat. $T_1$ map appears hypointense in striatum (str) and corpus callosum (cc) than that of cortex. The ventricle shows the highest intensity in $T_1$ due to elevated water content. In comparison, referring to FIG. 8B, the corresponding $T_2$ map appears reasonably homogeneous between striatum, corpus callosum and cortex except in the piriform cortex (pc) and ventricle. Referring to FIGS. 8C and 8D, MTR maps at labile frequency (3.5 ppm) and reference frequency (−3.5 ppm), respectively. Corpus callosum and striatum show hyperintense in both MTR(±3.5 ppm) maps, reflecting elevated magnetization transfer (MT) effects due to the presence of semisolid macromolecules and myelin. Moreover, MTR(−3.5 ppm) shows higher intensity in MTR(3.5 ppm), likely due to nuclear overhauser effect (NOE). Furthermore, the mean MTR map (i.e., MMTR=½*(MTR(3.5 ppm)+MTR(−3.5 ppm) and pH-sensitive $MTR_{asym}$ map are shown in FIGS. 8E and 8F, respectively. Whereas striatum and cc appear hyperintense in MTR images, they display hypointensity in pH-sensitive $MTR_{asym}$ map. It is noted that there is little pH difference between normal cerebral WM and GM, and the heterogeneity observed in $MTR_{asym}$ map is mainly attributable to the underlying macromolecular composition and microstructure differences instead of pH.

Figure 9A:
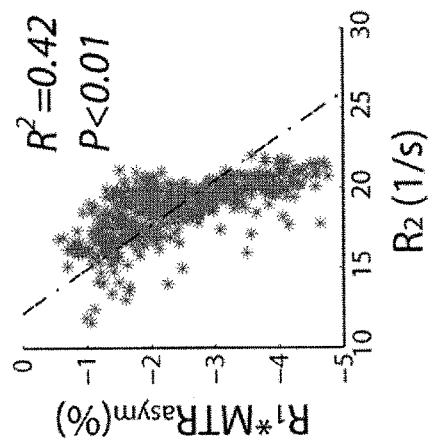
FIG. 9A is a graph showing correlation between $R_{1w}$-scaled $MTR_{asym}$ ($R_1*MTR_{asym}$) and $R_{1w}$.
Figure 9B:
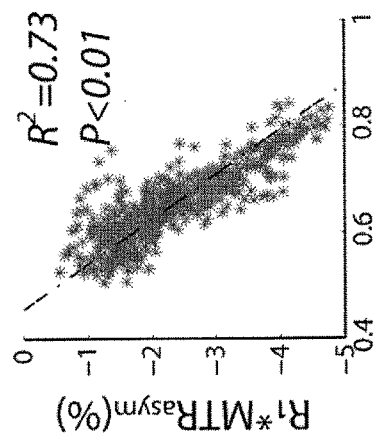
FIG. 9B is a graph showing correlation between $R_{1w}$-scaled $MTR_{asym}$ ($R_1*MTR_{asym}$) and $R_{2w}$.
Figure 9C:
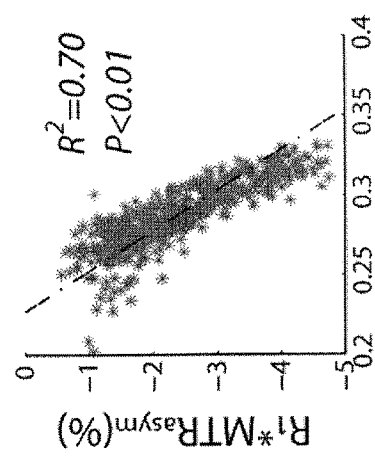
FIG. 9C is a graph showing correlation between $R_{1w}$-scaled $MTR_{asym}$ ($R_1*MTR_{asym}$) and MMTR.
Figure 9D:
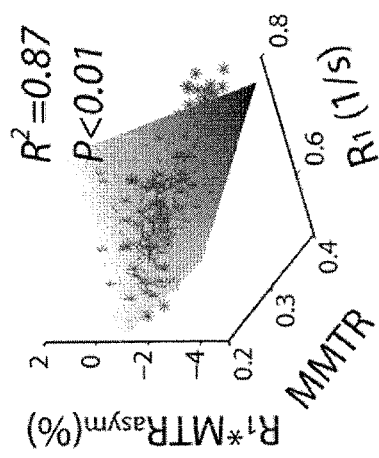
FIG. 9D is a three-axis graph showing the information of both FIGS. 9A and 9C plotted together.

Referring now to FIGS. 9A-9D, a series of graphs are provided to illustrate the association between $R_{1w}$, $R_{2w}$ and MMTR with pH-sensitive $MTR_{asym}$, per pixel. As can be seen in FIGS. 9A-9C, there was significant correlation between $R_{1w}$-scaled $MTR_{asym}$ ($R_1*MTR_{asym}$) and $R_{1w}$ (FIG. 9A), $R_{2w}$ (FIG. 9B) and MMTR (FIG. 9C). Also, FIG. 9D presents the information of FIGS. 9A and 9C plotted onto a three-dimensional graph. We found $R_1*MTR_{asym}$=5.4%–11.8%*$R_{1w}$ ($R^2$=0.73, P<0.01), $R_{1w}*MTR_{asym}$=3.8%–0.3%*$R_{2w}$ ($R^2$=0.38, P<0.01) and $R_1*MTR_{asym}$=9.0%–39.5%*MTTR ($R^2$=0.70, P<0.01). When analyzed for all normal animals, $R^2$ was found to be 0.68±0.06, 0.33±0.09 and 0.64±0.10 between $R_1*MTR_{asym}$ and $R_{1w}$, $R_{2w}$ and MMTR, respectively. We also evaluated multiple regression to enhance the prediction of $MTR_{asym}$. Notably, $R_{2w}$ was no longer a significant predicator in multiple regression analysis. We had $R_1*MTR_{asym}$=−12.7%+25.5%*$R_{1w}$+51.6%*MTTR−112.1%*MTTR*$R_{1w}$ ($R^2$=0.83, P<0.001, STATA). When analyzed for all normal animals, $R^2$ was found to be 0.80±0.07 for multiple regression analysis. This shows that substantial amount of the intrinsic heterogeneity in conventional $MTR_{asym}$ map can be explained by $T_{1w}$ and MTTR.

Figure 10C:
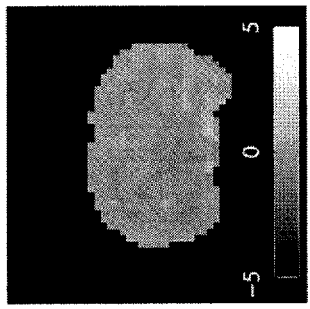
FIG. 10C is an image that shows the difference between experimentally measured and predicted $R_1$-scaled $MTR_{asym}$ map (ΔAPTR).
Figure 10B:
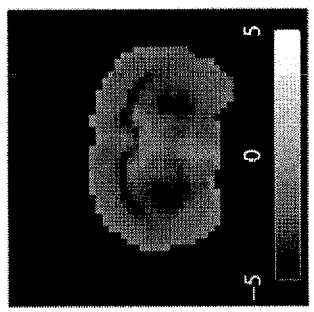
FIG. 10B is an image that shows $R_1$-scaled $MTR_{asym}$ map estimated from MMTR and $R_{1w}$.
Figure 10A:
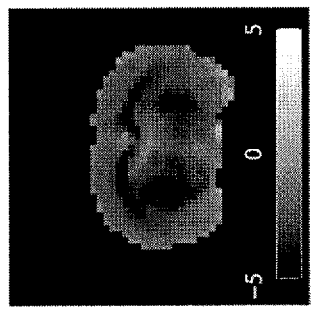
FIG. 10A is an image that shows an $R_{1w}$-scaled $MTR_{asym}$ map.

Turning to FIGS. 10A-10C, a set of images are provided to demonstrate correction of the intrinsic heterogeneity in APT MRI with multiple regression analysis of $T_{1w}$ and MMTR. FIG. 10A shows conventional $R_{1w}$-scaled $MTR_{asym}$ map. Because pH difference between normal brain WM and GM is very small, the heterogeneity observed in FIG. 10A is largely non-pH dependent. FIG. 10B shows $R_1$-scaled $MTR_{asym}$ map estimated from MMTR and $R_{1w}$, which reasonably agrees with the experimental measurement of FIG. 10A. Also, FIG. 10C shows the difference between experimentally measured and predicted $R_1$-scaled $MTR_{asym}$ map ($\Delta$APTR), which displays substantially reduced heterogeneity between brain WM and GM. Indeed, we calculated the contrast to noise ratio between striatum and cortex as $$CNR = \frac{\Delta RAPTR|_{cc} - \Delta RAPTR|_{str}}{\sqrt{(\sigma_{cc}^2 + \sigma_{str}^2)/2}},$$

where $\sigma$ is the standard deviation of each area of interest. We found CNR for the proposed $\Delta$RAPT MRI was 0.43±0.51, substantially smaller than that of conventional $R_1$-scaled $MTR_{asym}$ map, being 3.07±0.71 (P<0.01, paired t-test). Therefore, the proposed RAPT analysis substantially reduces heterogeneity in conventional $MTR_{asym}$ map, which may help resolve ischemia-induced tissue acidosis during acute stroke.

Figure 11A:
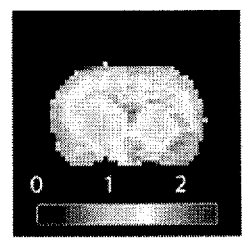
FIG. 11A is an image that shows show parametric $T_{1w}$ map in a rate with an acute ischemic stroke.
Figure 11B:
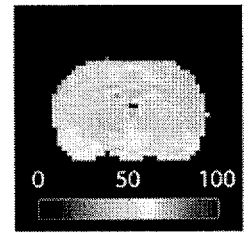
FIG. 11B is an image that shows show parametric $T_{2w}$ map in a rate with an acute ischemic stroke
Figure 11C:
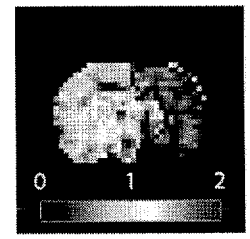
FIG. 11C is an CBF map that shows substantially reduced blood flow in the ipsilateral ischemic area of striatum and cortex.
Figure 11D:
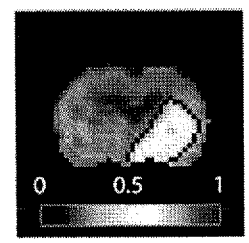
FIG. 11D is an image an ADC map showing noticeable ADC decrease only in striatum
Figure 11E:
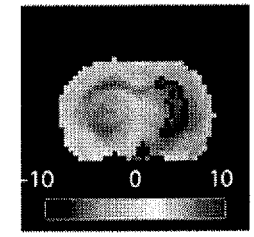
FIG. 11E is an image showing a pH-sensitive $MTR_{asym}$ map that displays hypointensity in the ipsilateral striatum.
Figure 11F:
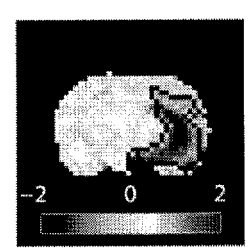
FIG. 11F is an image showing a ΔRAPTR map calculated by taking the difference between experimentally measured $R_{1w}*MTR_{asym}$ and that estimated based on multiple regression from the contralateral normal area.

Referring now to FIGS. 11A-11F, a series of images are provided that illustrate that the proposed RAPT MRI in acute ischemic stroke rates. In particular, FIGS. 11A and 11B show parametric $T_{1w}$ and $T_{2w}$ maps, respectively, with little change immediately following acute stroke. In FIG. 11C, a CBF map shows substantially reduced blood flow in the ipsilateral ischemic area of striatum and cortex. In comparison, as shown in FIG. 11D, diffusion MRI shows noticeable ADC decrease only in striatum. Ischemic lesions were determined with a threshold-based algorithm. Specifically, the threshold was calculated as two standard deviations beyond the mean, demonstrating substantial perfusion/diffusion lesion mismatch, as illustrated in the comparison of FIGS. 11C and 11D. On the other hand, as illustrated 11E, the pH-sensitive $MTR_{asym}$ map displays hypointensity in the ipsilateral striatum, the threshold-based algorithm could not faithfully detect the ischemic lesion due to the confounding intrinsic heterogeneity. In comparison, as shown in FIG. 11F, the $\Delta$RAPTR map can be calculated by taking the difference between experimentally measured $R_{1w}*MTR_{asym}$ and that estimated based on multiple regression from the contralateral normal area. Indeed, by minimizing non-pH dependent confounding factors, $\Delta$RAPTR enabled definition of acidic lesion.

FIG. 12 shows results of the multi-slice tissue segmentation algorithm in an acute stroke rat. Perfusion (FIG. 12A), pH-weighted RAPTR (FIG. 12B) and diffusion MRI (FIG. 12C) show heterogeneous acute ischemic tissue injury. Indeed, we found significance difference in perfusion (FIG. 12D), pH-weighted RAPT and diffusion lesions, being 297±73, 205±54 and 157±58 mm$^3$, respectively (P<0.05, repeated measures One-Way ANOVA).

The proposed RAPT MRI in acute ischemic stroke rates was evaluated with respect to substantially reduced CBF in the ipsilateral ischemic brain following intraluminal occlusion. In comparison, diffusion MRI showed noticeable ADC decrease in the striatum region. This shows that despite significant CBF drop in the lateral cortex, no substantial ADC change was measured. This indicated the presence of noticeable perfusion/diffusion lesion mismatch, suggesting heterogeneous ischemic tissue damage during acute stroke. In comparison, there was relatively small change in relaxation maps immediately following ischemia. On the other hand, pH-sensitive APT-weighted $MTR_{asym}$ map showed hypointensity in the ipsilateral striatum. However, CC and striatum regions in the contralateral normal region appeared hypointensive due to concomitant magnetization transfer (MT) and nuclear overhauser effects (NOE). This reduces the specificity of both $MTR_{asym}$ and RAPTR hypointensity to ischemic tissue acidosis. Using pixels in the contralateral normal brain, we found significant correlation between $R_1$ and RAPTR, per pixel ($R^2$=0.75, P<0.001), similar as what we found in normal animals. When analyzed for all normal animals (n=10), $R^2$ was found to be 0.63±0.12, significantly different from 0 (P<0.001, one sample t-test). The baseline RAPTR map can be estimated using the experimentally measured $T_1$ map and regression coefficients determined from the contralateral $T_1$ and RAPTR. Indeed, by subtracting the estimated RAPTR map from the experimentally measured RAPTR map, the non-APT effect can be largely removed, significantly enhancing the pH specificity of the proposed RAPT MRI method.

The present invention has been described in terms of one or more preferred embodiments, and it should be appreciated that many equivalents, alternatives, variations, and modifications, aside from those expressly stated, are possible and within the scope of the invention.

The invention claimed is:

1. A magnetic resonance imaging (MRI) system comprising:
    a magnet system configured to generate a polarizing magnetic field about at least a region of interest (ROI) of a subject arranged in the MRI system, the ROI including tissue believed to be pathological tissue;
    a plurality of gradient coils configured to apply a gradient field with respect to the polarizing magnetic field;
    a radio frequency (RF) system configured to apply RF excitation fields to the subject and a acquire MR image data therefrom; and
    a computer programmed to:
        i) control the plurality of gradient coils and the RF system to acquire diffusion kurtosis imaging (DKI) data from the ROI;
        ii) determine baseline correlation parameters from baseline MR data;
        iii) generate relaxation-normalized kurtosis data using the baseline correlation parameters to correct the DKI data at least for relaxation variations affecting kurtosis in the DKI data;
        iv) generate a report using the relaxation-normalized kurtosis data.

2. The system of claim 1 wherein the baseline correlation parameters include at least one of mean diffusivity (MD), fractional anisotropy (FA), and relaxation rates (R1, R2).

3. The system of claim 1 wherein the computer is further programmed to control the plurality of gradient coils and the RF system to acquire the baseline MR data from the subject at an ROI believed to not include the pathological tissue.

4. The system of claim 1 wherein generating the report includes generating a baseline kurtosis map using the baseline MR data and a corrected kurtosis map using the relaxation-normalized kurtosis data.

5. The system of claim 4 wherein the report includes at least one of a ratio of and a difference between the baseline kurtosis map and the corrected kurtosis map.

6. The system of claim 1 wherein generating the report includes performing a segmentation process to segment lesions in the ROI using the intrinsic heterogeneity corrected kurtosis data.

7. The system of claim 6 wherein the segmentation process includes applying a threshold to identify lesion with a relaxation-normalized kurtosis of more than two standard deviations from a mean.

8. The system of claim 7 wherein the mean is calculated from the baseline MR data.

9. The system of claim 8 wherein the baseline MR data is acquired from a contralateral normal brain.

10. The system of claim 6 wherein the lesions are ischemic kurtosis lesions.

11. A method for acquiring images of a region of interest (ROI) of a subject using a magnetic resonance imaging system, the method comprising:
    i) acquiring diffusion kurtosis imaging (DKI) data from tissue in the ROI believed to be pathological tissue;
    ii) acquiring baseline DKI data for tissue believed to not be pathological tissue;
    iii) determining correlation parameters from baseline DKI data;
    iv) generating corrected kurtosis data using the baseline correlation parameters by reducing relaxation-normalized in the DKI data; and
    iv) generating a report using the corrected kurtosis data.

12. The method of claim 11 wherein the baseline correlation parameters include at least one of mean diffusivity (MD), fractional anisotropy (FA), and relaxation rates (R1, R2).

13. The method of claim 11 wherein the baseline DKI data is acquired from the subject.

14. The method of claim 11 wherein generating the report includes performing a segmentation process to segment lesions in the ROI using the corrected kurtosis data.

15. The method of claim 14 wherein the lesions include ischemic kurtosis lesions.

16. A method for acquiring images of a region of interest (ROI) of a subject using a magnetic resonance imaging system, the method comprising:
    i) acquiring imaging data from tissue in the ROI believed to be pathological tissue;
    ii) acquiring baseline data from tissue in the subject believed to not be pathological tissue;
    iii) determining correlation parameters from the baseline data;
    iv) generating corrected data using the baseline correlation parameters that is corrected at least for intrinsic heterogeneity; and
    iv) generating a report using the corrected data.

17. The method of claim 16 wherein the baseline correlation parameters include at least one of mean diffusivity (MD), fractional anisotropy (FA), relaxation rates (R1, R2), magnetization transfer (MT), and chemical exchange saturation transfer (CEST)-based MRI.

18. The method of claim 16 the imaging data includes at least one of diffusion kurtosis imaging data, magnetization transfer (MT), chemical exchange saturation transfer (CEST), amide proton transfer (APT) and susceptibility weighted imaging (SWI)-based data.

19. The method of claim 16 wherein generating the report includes performing a segmentation process to segment lesions in the ROI using the corrected data.

20. The method of claim 16 wherein the segmentation process includes applying a threshold to identify lesion with a relaxation-normalized kurtosis of more than two standard deviations from a mean.

* * * * *